United States Patent
Zhou et al.

(10) Patent No.: US 11,642,105 B2
(45) Date of Patent: May 9, 2023

(54) ULTRASONIC TRANSDUCER, ULTRASONIC PROBE, AND ULTRASONIC DETECTION APPARATUS

(71) Applicant: EDAN INSTRUMENTS, INC., Shenzhen (CN)

(72) Inventors: Dan Zhou, Shenzhen (CN); Lulu Chen, Shenzhen (CN); Hua Luo, Shenzhen (CN); Jianhua Liu, Shenzhen (CN); Bo Ouyang, Shenzhen (CN); Jianhua Mo, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 183 days.

(21) Appl. No.: 17/120,235

(22) Filed: Dec. 13, 2020

(65) Prior Publication Data

US 2021/0093296 A1  Apr. 1, 2021

Related U.S. Application Data

(63) Continuation of application No. PCT/CN2018/090889, filed on Jun. 12, 2018.

(51) Int. Cl.
*A61B 8/00* (2006.01)
*B06B 1/06* (2006.01)

(52) U.S. Cl.
CPC .......... *A61B 8/4494* (2013.01); *A61B 8/4444* (2013.01); *A61B 8/546* (2013.01); *B06B 1/0607* (2013.01)

(58) Field of Classification Search
CPC ..... A61B 8/4494; A61B 8/4444; A61B 8/546; A61B 8/4483; A61B 8/00; B06B 1/0607; B06B 1/0629; B06B 1/0677
See application file for complete search history.

(56) References Cited

U.S. PATENT DOCUMENTS

| 5,555,887 A | 9/1996 | Fraser et al. |
| 5,602,718 A | 2/1997 | Peszynski et al. |

(Continued)

FOREIGN PATENT DOCUMENTS

| CN | 1859871 A | 11/2006 |
| CN | 102098965 A | 6/2011 |

(Continued)

OTHER PUBLICATIONS

International search report,PCT/CN2018/090889, dated Aug. 1, 2019 (4 pages).

(Continued)

*Primary Examiner* — Jason M Ip
*Assistant Examiner* — Renee C Langhals (57) ABSTRACT

An ultrasonic transducer (200) includes: a piezoelectric vibrator assembly (10), an acoustic matching layer (20), a heat sink (30), and an acoustic absorption layer (40). The heat sink (30) comprises a body (31), and a head portion (32) and a tail portion (33). The body (31) has a central axis extending in a direction from the head portion (32) to the tail portion (33). A surface of the tail portion (33) of the heat sink (30) disposed away from the head portion (32) is a first surface (331). The first surface (331) is an oblique surface or a tapered surface. The angle between the first surface (331) and the central axis is an acute angle. The acoustic absorption layer (40) at least covers the first surface (331).

20 Claims, 10 Drawing Sheets

(56) References Cited

U.S. PATENT DOCUMENTS

| | | | |
|---|---|---|---|
| 5,721,463 A | 2/1998 | Snyder et al. | |
| 2004/0002655 A1 | 1/2004 | Bolorforosh et al. | |
| 2011/0114303 A1* | 5/2011 | Rhim | G10K 11/004 165/185 |
| 2014/0100561 A1* | 4/2014 | Biadillah | A61B 18/1492 606/33 |
| 2015/0270474 A1 | 9/2015 | Osawa | |
| 2017/0167716 A1* | 6/2017 | Ezaki | C08L 67/02 |
| 2018/0028159 A1* | 2/2018 | Hageman | A61B 8/4483 |
| 2018/0290176 A1* | 10/2018 | Fukase | B06B 1/0685 |

FOREIGN PATENT DOCUMENTS

| | | |
|---|---|---|
| CN | 104722469 A | 6/2015 |
| CN | 206924084 U | 1/2018 |
| CN | 209332093 U | 9/2019 |
| CN | 209474649 U | 10/2019 |
| CN | 210170071 U | 3/2020 |
| CN | 210170072 U | 3/2020 |
| CN | 110960252 A | 4/2020 |
| CN | 110960253 A | 4/2020 |
| CN | 110960257 A | 4/2020 |
| CN | 110960258 A | 4/2020 |
| WO | WO2010011034 A1 | 1/2010 |
| WO | WO2015029637 A1 | 3/2015 |
| WO | WO2020062258 A1 | 4/2020 |
| WO | WO2020062259 A1 | 4/2020 |
| WO | WO2020062270 A1 | 4/2020 |
| WO | WO2020062272 A1 | 4/2020 |

OTHER PUBLICATIONS

European search report, European application No. 18922239.1, dated Nov. 5, 2021 (9 pages).

* cited by examiner

ULTRASONIC TRANSDUCER, ULTRASONIC PROBE, AND ULTRASONIC DETECTION APPARATUS

CROSS REFERENCE TO RELATED APPLICATIONS

This application is a continuation-application of International (PCT) Patent Application No. PCT/CN2018/090889 filed on Jun. 12, 2018, the content of which is herein incorporated by reference in its entirety.

TECHNICAL FIELD

The present disclosure relates to the technical field of ultrasonic applications, and in particular, to an ultrasonic transducer, an ultrasonic probe, and an ultrasonic detection apparatus.

BACKGROUND

In related technologies, ultrasonic probes are widely used in the fields of medical diagnosis, industrial detection, and underwater acoustics. The ultrasonic probes adopt ultrasonic transducers as functional components, use piezoelectric vibrators of the ultrasonic transducers to detect ultrasonic signals, convert the ultrasonic signals into electrical signals, and finally visualize the electrical signals and display images. To meet requirements of the application of ultrasound imaging, a large number of piezoelectric vibrators are required to form an array, and the piezoelectric vibrators actively transmit the ultrasonic signals and then receive reflected echoes during the transmission of the ultrasonic signals. Especially in phased-array ultrasound imaging technology, numerous piezoelectric vibrators (array) are almost simultaneously excited by electrical pulses and resonate to generate ultrasonic waves, besides, heat is also generated at the same time. During the operation, the piezoelectric vibrators of a phased-array probe generate heat significantly. If the accumulative heat cannot be effectively diffused, a temperature of the probe will rise.

In this way, on one hand, since medical diagnosis has regulatory requirements for a temperature rising of the probe when the probe touches a human body, the specific application of the ultrasonic probes will be limited. On the other hand, a high temperature rising will also cause a large drift in performance and parameters of the probe, which affects detection results, such that the detection results are inaccurate. In addition, the higher temperature rising may also cause an accelerated aging or even failure of materials, structures, and components of the probe.

However, in the related art, the heat-dissipation effect is poor, and ultrasonic energy will return back to the piezoelectric vibrator of the ultrasonic transducer and cause interference to the piezoelectric vibrator.

SUMMARY

The present disclosure proposes an ultrasonic transducer. The present disclosure also provides an ultrasonic probe including the ultrasonic transducer and an ultrasonic detection apparatus including the ultrasonic probe.

According to some embodiments of a first aspect of the present disclosure, the ultrasonic transducer includes: a piezoelectric-vibrator assembly, having a first side and a second side and comprising one or more piezoelectric vibrators; an acoustic matching layer, arranged on the first side of the piezoelectric-vibrator assembly; a heat sink, arranged on the second side of the piezoelectric-vibrator assembly and comprising: a body, having a central axis; a head portion, disposed at one end of the body and facing towards the piezoelectric-vibrator assembly; and a tail portion, disposed at another end of the body opposite to the head portion and facing away from the piezoelectric-vibrator assembly, wherein the central axis extends in a direction from the head portion to the tail portion; the tail portion comprises a first surface disposed at one side of the tail portion facing away from the head portion, the first surface is an oblique surface or a tapered surface, and an angle between the first surface and the central axis is an acute angle; and an acoustic-absorption layer, covering at least the first surface.

In some embodiments, the oblique surface comprises at least one inclined sub-surface, and an angle between each of the at least one inclined sub-surface and the central axis of the body is an acute angle.

In some embodiments, the oblique surface comprises a pair of inclined sub-surfaces intersecting with each other at a straight line and gradually extending away from each other in a direction from the tail portion to the head portion, an angle between the pair of inclined sub-surfaces is an acute angle, and an angle between each of the pair of inclined sub-surfaces and the central axis of the body is an acute angle.

In some embodiments, the oblique surface is a pyramid surface comprising a plurality of sub-surfaces, and an angle between each of the plurality of sub-surfaces and the central axis is an acute angle.

In some embodiments, the tapered surface is a conical surface having a generatrix, an angle between the generatrix of the conical surface and the central axis is less than 90 degrees.

In some embodiments, the tail portion comprises an outer face, the outer face of the tail portion comprises the first surface, and the acoustic-absorption layer at least covers the outer face of the tail portion.

In some embodiments, the acoustic-absorption layer covers the outer face of the tail portion, an outer face of the body, and a side wall of the head portion.

In some embodiments, the acoustic-absorption layer covers an outer face of the heat sink.

In some embodiments, the heat sink is made of any material selected from the group consisting of monocrystal alumina, monocrystal silicon, and monocrystal silicon carbide.

In some embodiments, a distance between the second side of the heat sink and the piezoelectric-vibrator assembly is defined as δ, wherein 0≤δ≤3 mm.

In some embodiments, the head portion comprises a second surface disposed at an end of the head portion facing away from the tail end, the acoustic-absorption layer further covers the second surface, and the second surface is spaced from the second side of the piezoelectric-vibrator assembly via the acoustic-absorption layer.

In some embodiments, the head portion comprises a plurality of heat-dissipation portions extending toward the piezoelectric-vibrator assembly, the plurality of heat-dissipation portions are spaced apart from each other, and the acoustic-absorption layer comprises an acoustic-absorption protrusion disposed in a gap defined between every two adjacent heat-radiating portion.

In some embodiments, the heat sink is made of polycrystalline material.

In some embodiments, the acoustic-absorption layer completely covers an outer face of the heat sink.

In some embodiments, a distance between the second side of the heat sink and the piezoelectric-vibrator assembly is defined as δ, wherein 0≤δ≤3 mm.

In some embodiments, the acoustic-absorption layer comprises a side wall covering the first surface of the heat sink, and the head portion further comprises a second surface disposed at an end facing away from the tail portion, the side wall comprises an outer face facing away from the tail portion, and the outer face of the side wall is parallel to the second surface.

In some embodiments, the acoustic-absorption layer comprises a flexible substrate and particles filled in the flexible substrate. The flexible substrate is made of any one selected from the group consisting of epoxy, polyurethane, and silicone. The particles are selected from the group consisting of tungsten powders and lead powders.

According to some embodiments of a second aspect of the present disclosure, the ultrasonic probe includes the ultrasonic transducer, comprising: a piezoelectric-vibrator assembly, having a first side and a second side opposite to the first side and comprising one or more piezoelectric vibrators; an acoustic matching layer, arranged on the first side of the piezoelectric-vibrator assembly; a heat sink, arranged on the second side of the piezoelectric-vibrator assembly and comprising: a body; a head portion, disposed at one end of the body and facing towards the piezoelectric-vibrator assembly; and a tail portion, disposed at another end of the body opposite to the head portion and facing away from the piezoelectric-vibrator assembly, wherein the tail portion comprises a first surface disposed at one side of the tail portion facing away from the head portion, and the first surface is an oblique surface or a tapered surface; and an acoustic-absorption layer, covering at least the first surface.

In some embodiments, the ultrasonic probe includes: a housing; and an acoustic window, connected to the housing, wherein the acoustic window and the housing cooperatively define a receiving cavity, and the ultrasonic transducer is received in the receiving cavity.

According to some embodiments of a third aspect of the present disclosure, the ultrasonic detection apparatus includes the ultrasonic probe as previously described.

The additional aspects and advantages of the present disclosure will be partly given in the following description, and part will become obvious from the following description, or be understood through the practice of the present disclosure.

REFERENCE NUMERALS

Ultrasonic probe 100, ultrasonic transducer 200;
piezoelectric-vibrator assembly 10, piezoelectric vibrator 11, first side 12, second side 13;
acoustic matching layer 20;
heat sink 30, body 31, head portion 32, second surface 321, heat sink 322, tail portion 33, first surface 331;
acoustic-absorption layer 40, acoustic-absorption protrusion 41, side wall 42;
acoustic window 50;
housing 60.

DETAIL PORTIONED DESCRIPTION

Embodiments of the present disclosure are described in detail portion below. Examples of the embodiments are shown in the accompanying drawings, in which same or similar reference numerals indicate same or similar elements or elements with same or similar functions. The embodiments described below with reference to the accompanying drawings are exemplary, and are intended to explain the present disclosure, but should not be construed as limiting the present disclosure.

An ultrasonic probe 100 and an ultrasonic transducer 200 according to some embodiments of the present disclosure will be described below with reference to FIGS. 1 to 8.

Figure 1:
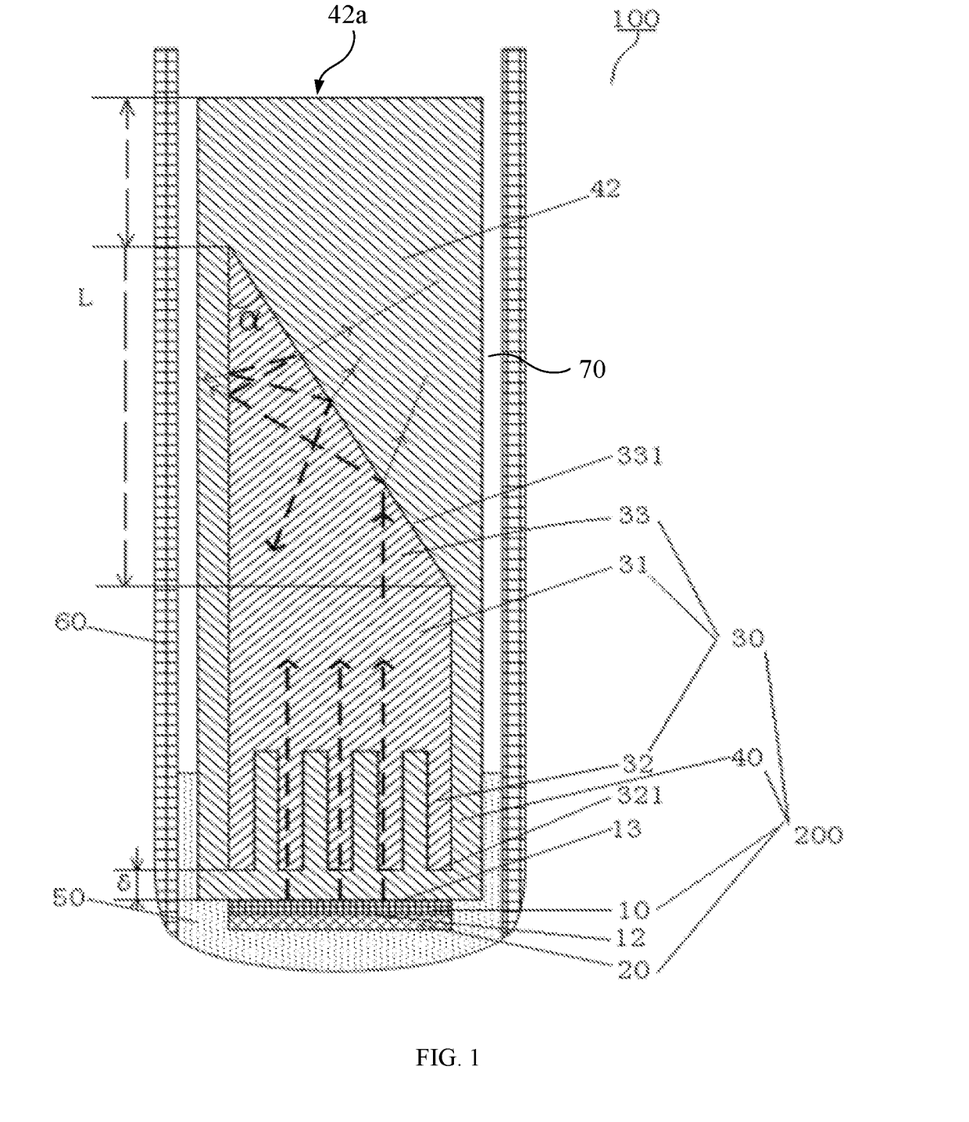
FIG. 1 is a schematic view of an ultrasonic probe according to some embodiments of the present disclosure.
Figure 2:
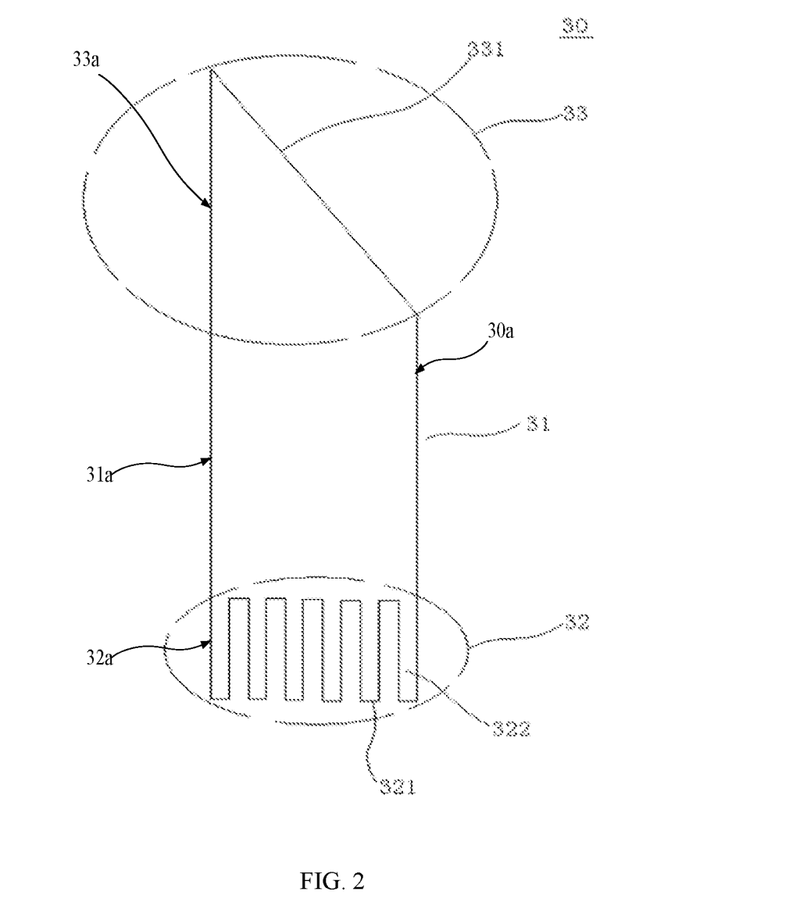
FIG. 2 is a schematic view of a heat sink of the ultrasonic probe according to some embodiments of the present disclosure.

As shown in FIGS. 1 and 2, in some embodiments of the first aspect of the present disclosure, the ultrasonic transducer 200 may include a piezoelectric-vibrator assembly 10, an acoustic matching layer 20, a heat sink 30, and an acoustic-absorption layer 40.

The piezoelectric-vibrator assembly 10 may have a first side 12 and a second side 13. As shown in FIG. 1, the second side 13 may be disposed opposite to the first side 12. The piezoelectric-vibrator assembly 10 may include one or more piezoelectric vibrators 11. More specifically, each of the one or more piezoelectric vibrators 11 may be implemented as a wafer with a good piezoelectric effect or a piezoelectric ceramic. When receiving an electrical pulse, each of the one or more piezoelectric vibrators 11 may generate a mechanical ultrasonic vibration to emit ultrasonic waves, and may further receive the reflected ultrasonic waves and convert ultrasonic signals of the ultrasonic waves into electrical signals.

In case that the number of the one or more piezoelectric vibrators 11 is two or more, that is, in case that a plurality of piezoelectric vibrators 11 are provided, the plurality of piezoelectric vibrators 11 may be arranged in a row along a straight line, such that the ultrasonic probe 100 may be configured as a linear array probe. In some embodiments, the plurality of piezoelectric vibrators 11 may also be arranged in an arc, such that the ultrasonic probe 100 may be configured as a convex array probe. In some embodiments, the plurality of piezoelectric vibrators 11 may also be arranged in a matrix array, such that the ultrasonic probe 100 may be configured as a matrix array probe.

In some embodiments, the acoustic matching layer 20 may be arranged on the first side 12 of the piezoelectric-vibrator assembly 10. The acoustic matching layer 20 may be configured to transmit as much ultrasonic energy as possible to the medium to be measured.

The heat sink 30 may be arranged on the second side 13 of the piezoelectric-vibrator assembly 10. The heat sink 30 may include a body 31, a head portion 32, and a tail portion 33. In some embodiments, the head portion 32 and the tail portion 33 may be located at two opposite ends of the body 31. The body 31 may be substantially in shape of a cylinder or a column and may have a central axis C1 extending in a direction from the head portion 32 to the tail portion 33. The head portion 32 of the heat sink 30 may face towards the piezoelectric-vibrator assembly 10, while the tail portion 33 may face away from the piezoelectric-vibrator assembly 10. The tail portion 33 of the heat sink 30 may include a first surface 331 facing away from the head portion 32. The first surface 331 may be an oblique surface or a tapered surface. An angle between the first surface 331 and the central axis C1 may be an acute angle. The acoustic-absorption layer 40 may cover at least the first surface 331. In the embodiments described above, the body 31 may be in shape of a column. However, in other embodiments, the body 31 may be in other shapes, as long as the body 31 has the central axis extending in the direction from the head portion 32 to the tail portion 33.

The heat sink 30 may include a thermally-conductive material with low acoustic impedance, such as graphite, aluminum, or the like. The acoustic-absorption layer 40 may include a material with better acoustic absorption and noise reduction effects.

It should be noted that, the first surface 331 may refer to a surface located at the tail portion 33 of the heat sink 30 and facing towards the head portion 32 in the axial direction of the body 31. In this way, most of the ultrasonic waves emitted by the one or more piezoelectric vibrators 11 disposed on the head portion 32 may preferentially or tend to contact with the first surface 331 during the transmission toward the tail portion 33, and be further refracted or reflected by the first surface 331.

In the ultrasonic transducer 200 according to some embodiments of the present disclosure, the first surface 331 may be processed into an oblique surface or a tapered surface, and at least the first surface 331 may be wrapped with the acoustic-absorption layer 40. In this way, when the ultrasonic energy entering the heat sink 30 is transmitted to the tail portion 33, the ultrasonic energy may undergo multiple reflections and refractions at the tail portion 33 and may be fully absorbed by the acoustic-absorption layer 40 disposed on the surface (at least the first surface 331) of the heat sink 30. Therefore, the ultrasonic energy will no longer return back to the one or more piezoelectric vibrators 11, and it is possible to avoid or reduce the interference on the one or more piezoelectric vibrators 11. Therefore, compared with the heat sink in the related art, the head portion 32 of the heat sink 30 may be disposed closer to the one or more piezoelectric vibrators 11 or even directly contact with the one or more piezoelectric vibrators 11 in distance. In this way, the heat sink 30 may cool down the one or more piezoelectric vibrators 11 more significantly, and a good heat-dissipation effect may be achieved.

The first surface 331 may be in various shapes. Four types of the first surface 331 may be listed below.

Figure 3:
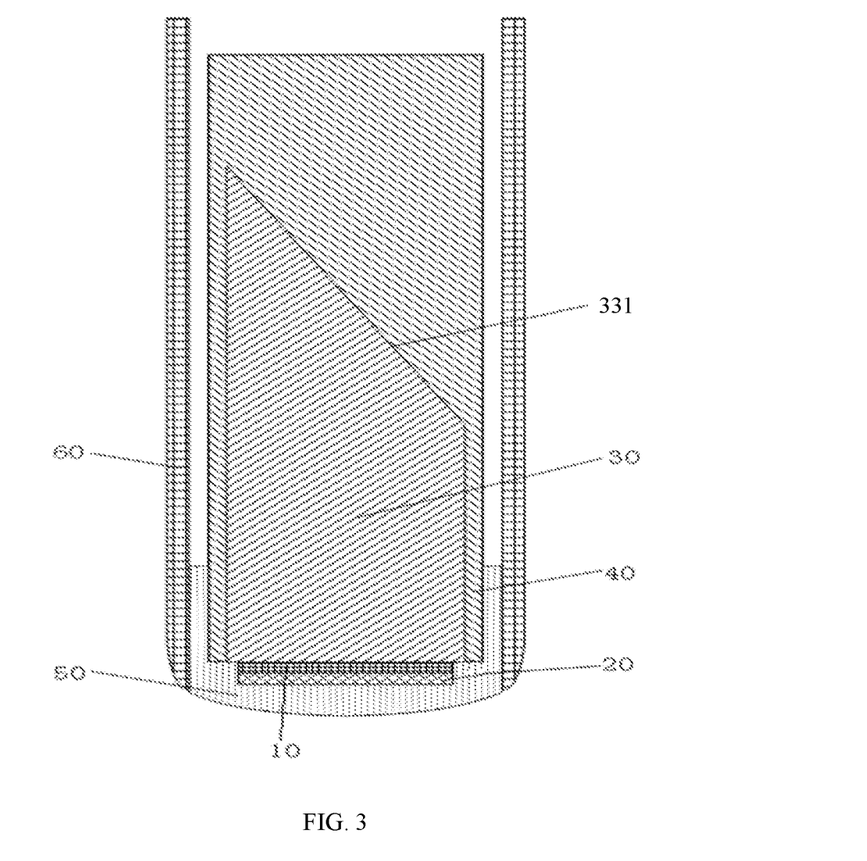
FIG. 3 is a schematic view of an ultrasonic probe according to some embodiments of the present disclosure.
Figure 4:
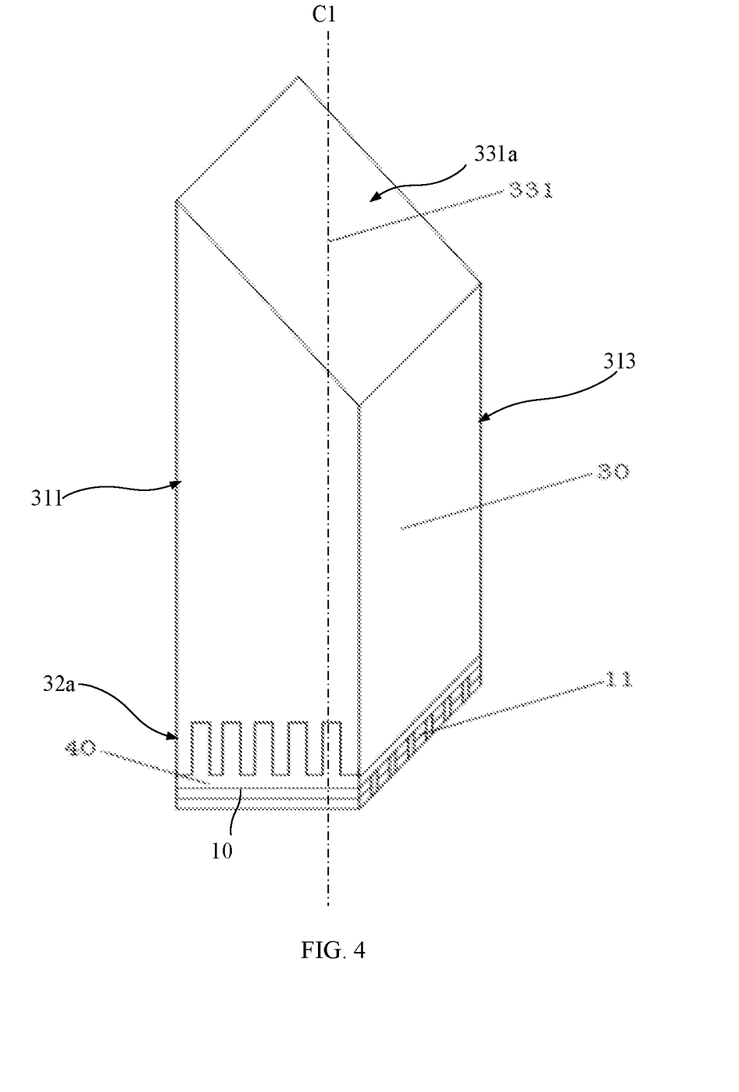
FIG. 4 is a partial schematic view of an ultrasonic transducer according to some embodiments of the present disclosure.
Figure 5:
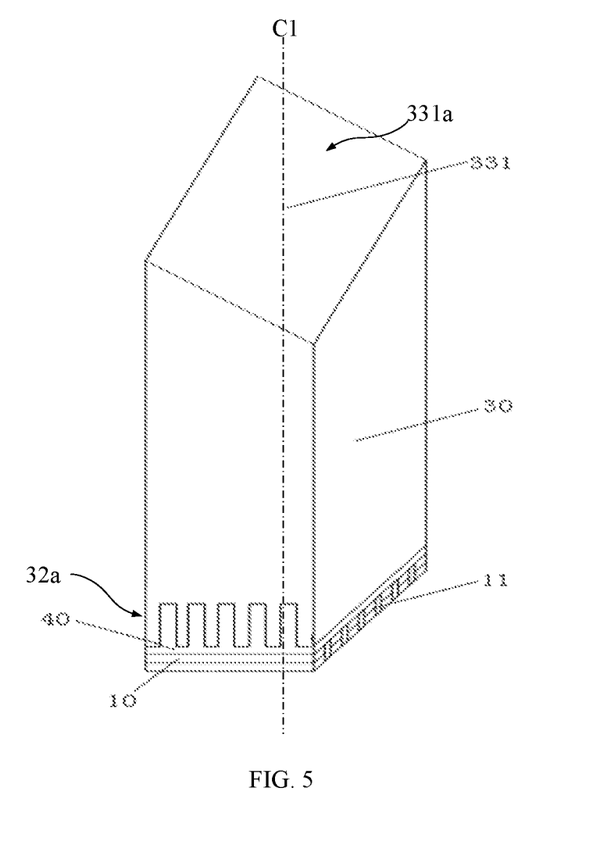
FIG. 5 is a partial schematic view of an ultrasonic transducer according to some embodiments of the present disclosure.

In some embodiments, the first surface 331 may be the oblique surface and may include at least one inclined sub-surface 331a, and an angle between the at least one inclined sub-surface 331a and the central axis C1 of the body 31 may be an acute angle. In some embodiments as shown in FIGS. 3 and 4, when the number of the first surface 331 is one, the one or more piezoelectric vibrators 11 may emit ultrasonic waves towards the inclined sub-surface. When the ultrasonic waves firstly contact with the inclined sub-surface 331a, a part of the ultrasonic waves may be refracted out of the heat sink 30, and may be further absorbed by the acoustic-absorption layer 40 covering the inclined sub-surface 331a. The other part of the ultrasonic waves may be reflected in the heat sink 30 and transmitted toward a side wall 32a of the head portion 32. A part of the ultrasonic waves transmitted to the side wall 32a of the head portion 32 may be refracted and the other part may be reflected toward the inclined sub-surface 331a, and so on. The ultrasonic waves which are not transmitted out of the heat sink 30 may be reflected for multiple times by the inclined sub-surface 331a and the side wall 32a of the head portion 32. In this way, the ultrasonic energy may be significantly weakened during the above processes, such that few ultrasonic energy may be finally transmitted toward the head portion 32 of the heat sink, thereby avoiding or reducing the interference on the one or more piezoelectric vibrator 11.

The body 31 of the heat sink 30 shown in FIG. 4 may be substantially in shape of a square pillar or column. An angle between the inclined sub-surface 331a and a side wall 311 of the body 31 may be substantially equal to an angle between the inclined sub-surface 331a and an opposite side wall 313 of the body 31. Differences between the embodiments shown in FIG. 5 and that shown in FIG. 4 may lie in that, inclination directions of the inclined sub-surfaces 331a in the two embodiments may be different (that is, lines perpendicular to the two inclined sub-surfaces may be not parallel to or overlap with each other).

Of course, the present disclosure may be not limited to this. The number of inclined sub-surfaces 331a may be one or more. The inclined sub-surface 331a may also face towards different directions and form at different angles from the central axis. In addition, the first surface 331 may be a single-sided inclined sub-surface, a double-sided inclined sub-surface, or even multi-sides inclined sub-surface. That is to say, the first surface 331 may include one inclined sub-surface, two inclined sub-surfaces, or three or more inclined sub-surfaces.

Figure 6:
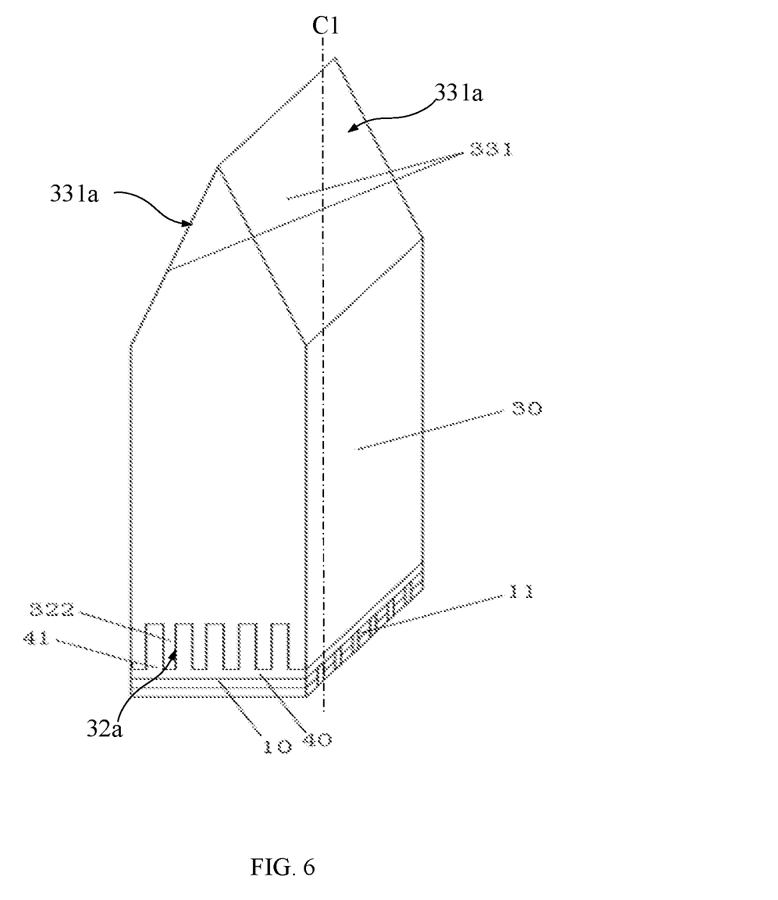
FIG. 6 is a partial schematic view of an ultrasonic transducer according to some embodiments of the present disclosure.
Figure 7:
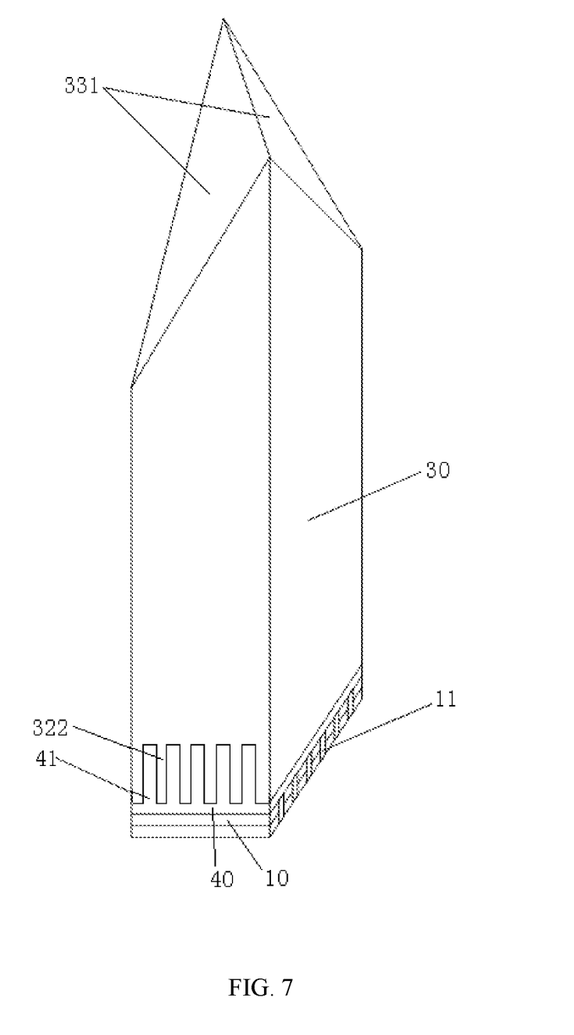
FIG. 7 is a partial schematic view of an ultrasonic transducer according to some embodiments of the present disclosure.

In some embodiments shown in FIGS. 6 and 7, the first surface 331 may include: a pair of inclined sub-surfaces 331a intersecting with each other at a straight line and gradually extending away from each other in a direction from the tail portion 33 to the head portion 32. An angle between the pair of inclined sub-surfaces 331a may be an acute angle. An angle between each of the pair of inclined sub-surfaces 331a and the central axis C1 of the body 31 may be an acute angle.

More specifically, the body 31 may be substantially in shape of a square pillar or column. The pair of inclined sub-surfaces 331a may intersect with each other, such that the tail portion 33 may be in shape of a sharp angle. The pair of inclined sub-surfaces 331a may be substantially perpendicular to two opposite side walls of the heat sink 30. The angle between the pair of inclined sub-surfaces 331a and the central axis C1 of the body 31 may be substantially equal to each other. The pair of inclined sub-surfaces 331a may be defined as a first inclined sub-surface and a second inclined sub-surface. In this way, a part of the one of more piezoelectric vibrators 11 facing towards the first inclined sub-surface may emit ultrasonic waves toward the first inclined sub-surface. After the ultrasonic waves firstly contact with the first inclined sub-surface, a part of the ultrasonic waves may be refracted out of the heat sink 30 and absorbed by the acoustic-absorption layer 40 covering on the first inclined sub-surface. The other part of the ultrasonic waves may be transmitted to the second inclined sub-surface. A part of the ultrasonic waves transmitted to the second inclined sub-surface may be refracted and the other part may be transmitted toward the first inclined sub-surface, and so on. In this way, the ultrasonic waves which are not transmitted out of the heat sink 30 may be reflected by the pair of inclined sub-surfaces 331a of the tail portion 33 and the side wall for multiple times, and the ultrasonic energy may be significantly weakened during the above processes. Similarly, those skilled in the art may deduce the transmission path of the ultrasonic waves emitted by the piezoelectric vibrator 11 facing towards the second inclined sub-surface according to the above description, which may be not repeated here.

Difference between some embodiments shown in FIG. 6 and some embodiments shown in FIG. 7 may lie in that: the first inclined sub-surface and the second inclined sub-surface in some embodiments shown in FIG. 6 may be both substantially quadrangular, while a third inclined sub-surface and a fourth inclined sub-surface in some embodiments shown in FIG. 7 may be substantially triangular. Of course, the reason for the differences in the shape of the inclined sub-surfaces in these two embodiments may be the inclined angles and the setting positions of inclined sub-surfaces are different.

In the embodiments described in FIGS. 4-7, the inclined sub-surface(s) of the first surface 331 may have a first vertex connected to or located in a side edge of the body 31, and a second vertex located in another side edge of the body or connected to another inclined sub-surface. The first vertex is located at a first position, while the second vertex is located at a second position, and the first position is lower than the second portion in a direction from the head portion 32 to the tail portion 33, and the inclined sub-surface continuously extends or rises from the first vertex to the second vertex.

Figure 8:
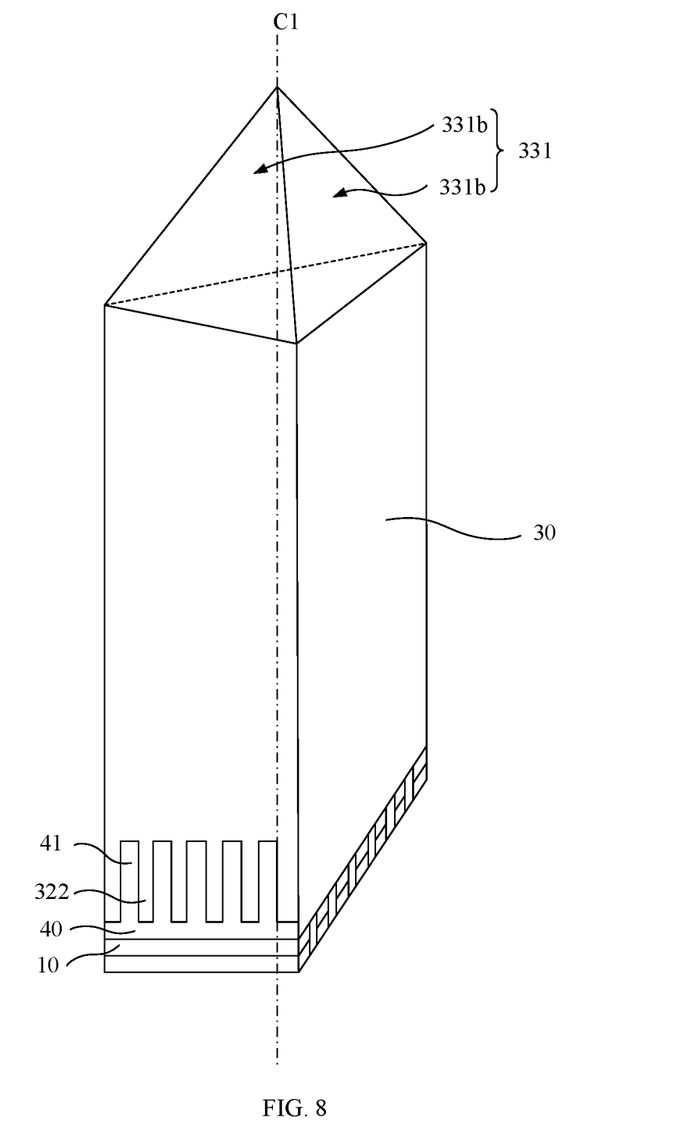
FIG. 8 is a partial schematic view of an ultrasonic transducer according to some embodiments of the present disclosure.

Of course, in other embodiments, the first surface 331 may be the oblique surface and the oblique surface may also be a pyramid surface, as shown in FIG. 8. The pyramid surface may include a plurality of sub-surfaces 331b. An angle between each of the plurality of sub-surfaces 331b of the pyramid surface and the central axis C1 may be an acute angle. In other words, the tail portion 33 in some embodiments as shown in FIG. 4 may be further sharpened to obtain a pyramidal surface. In this way, a part of the ultrasonic waves firstly transmitted to any one of the plurality of sub-surfaces 331b of the pyramid surface may be transmitted out of the heat sink 30 and may be absorbed by the acoustic-absorption layer 40 covering the corresponding sub-surface. The other part of the ultrasonic waves may be transmitted to the remaining sub-surfaces of the pyramidal surface. In this way, the ultrasonic waves inside the heat sink 30 may be reflected for multiple times between various sub-surfaces of the pyramidal surface, and the ultrasonic energy may be significantly weakened.

It may be understandable that the pyramid surface may be a triangular pyramid surface (as shown in FIG. 8), a quadrangular pyramid surface, or the like. The number of the sub-surfaces of the pyramid surface may be three or more. Each sub-surface of the pyramid surface may be substantially flat.

Figure 9:
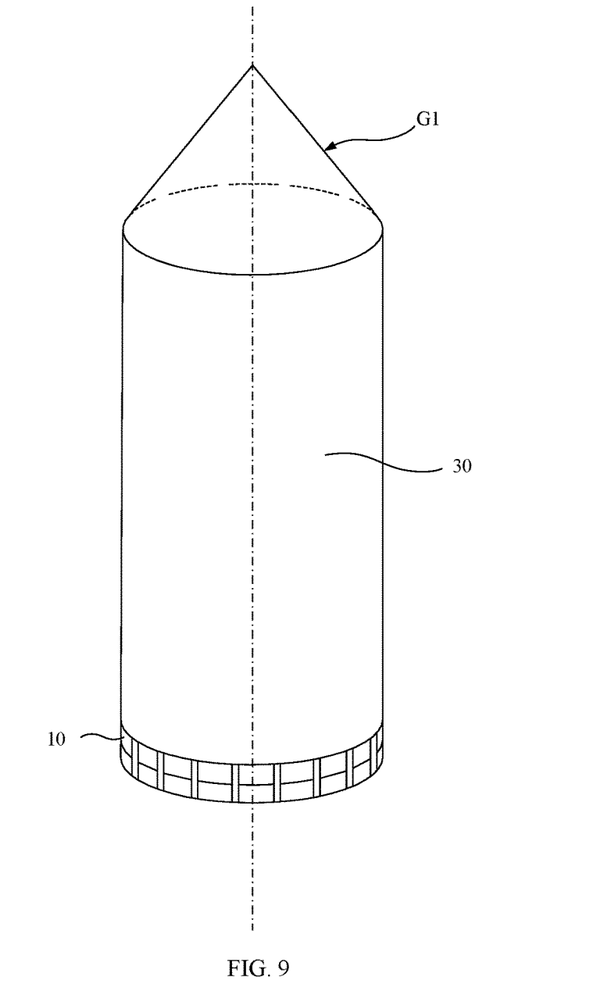
FIG. 9 is a partial schematic view of an ultrasonic transducer according to some embodiments of the present disclosure.

In some embodiments, the first surface 331 may be a tapered surface and specifically a conical surface, as shown in FIG. 9. An apex angle of each cross section passing through a vertex of the conical surface and coinciding with the central axis C1 may be less than 90 degrees. In some embodiments, the conical surface may have a generatrix G1, an angle between the generatrix G1 of the conical surface and the central axis C1 is less than 90 degrees. In this way, a part of the ultrasonic waves firstly transmitted to the conical surface may be transmitted out of the heat sink 30 and may be absorbed by the acoustic-absorption layer 40 covering the conical surface, and the other part of the ultrasonic waves may undergo multiple reflections within the conical surface. Thus, the ultrasonic energy may be significantly weakened.

It should be noted that, the shape of the body 31 of the heat sink 30 may be not limited to the square column shown in the drawings, and may also be a cylinder, a prism, or the like.

As further shown in FIG. 1, an angle $\alpha$ between the first surface 331 of the tail portion 33 and the central axis may be defined as a. The applicant may have found through research that, the smaller the angle $\alpha$ of the first surface of the tail portion 33 of the heat sink 30 is, the more times the ultrasonic waves may be reflected at the tail portion 33, and the more ultrasonic energy may be consumed.

Taking FIG. 1 as an example, when $\alpha<90°/N$, the ultrasonic waves may undergo $(2N-1)$ times of reflections at the tail portion 33, wherein N is a natural number. The smaller the $\alpha$ is, that is, the larger the corresponding N is, the more the number of times of reflections $(2N-1)$ may occur at the tail portion 33, and the more ultrasonic energy may be consumed. Therefore, in case that the configuration is allowed in the internal space of the ultrasonic probe 100, the smaller the angle of the first surface, the better the implementation effect.

Of course, the structure of the tail portion 33 of the heat sink 30 may be not limited to the above description, and may be other similar structures in which multiple times of reflections occur to consume the ultrasonic energy. In this way, since the ultrasonic energy entering the heat sink 30 may be at least partially or even completely consumed at the tail portion 33 and no longer return back to cause signal interference, the heat sink 30 may be disposed closer to the piezoelectric vibrator 11 which is deemed as a main heat source of the ultrasonic transducer 200 in structure, and the heat of the electric vibrator 11 may be rapidly diffused by the heat sink 30 to avoid or reduce the possibility of excessive rising of the local temperature.

To enhance the absorption effect, it is possible to enlarge a covering area of the acoustic-absorption layer 40. That is, the acoustic-absorption layer 40 may be attached to not only the oblique surface or the tapered surface at the tail portion 33 of the heat sink 30, but also cover other surfaces of the heat sink 30. In some embodiments shown in FIG. 1, the acoustic-absorption layer 40 may completely cover an outer face 30a of the heat sink 30. Herein, the outer face 30a of the heat sink 30 may at least include an outer face 33a of the tail portion 33, an outer face 31a of the body 31, a side wall 32a of the head portion 32, and a second surface 321 of the head portion 32 which faces away from the tail portion 33. Herein, the outer face 33a of the tail portion 33 may include at least the first surface 331.

When the material of the heat sink 30 is uniform and dense, such as monocrystal alumina, monocrystal silicon, monocrystal silicon carbide, or the like, there may be almost no weak scattering caused by defects such as crystalline grains or pores in the material during the transmission of the ultrasonic waves. In this case, the acoustic-absorption layer 40 does not need to be wrapped on a front end (including such as the head portion 32) of the heat sink 30 to eliminate the scattered noise. Thus, an end surface of the front end (for example, the second surface 321 of the head portion 32) of the heat sink 30 may directly contact with a surface of an acoustic stack (including the piezoelectric vibrator 11, the matching layer 20, or the like). In this way, it is possible to achieve a better heat-dissipation effect.

For example, in some embodiments shown in FIG. 2, the acoustic-absorption layer 40 may cover the outer face 33a of the tail portion 33, the outer face 31a of the body 31, and the side wall 32a of the head portion 32. Furthermore, an end surface (that is, the second surface 321) of the head portion 32 of the heat sink 30 may be flat and may be adhered to the second side 13 of the piezoelectric-vibrator assembly 10.

On the contrary, in case that the heat sink 30 is made of polycrystalline material or there are many defects inside the heat sink 30, the internal crystalline grains and defects will cause the weak scattering of ultrasonic energy which may result in a returning back of noise signals. In this case, the front end of the heat sink 30 may be also wrapped with the acoustic-absorption layer 40 of a certain thickness to eliminate the weak noise signals. As shown in FIG. 1, the acoustic-absorption layer 40 may be also coated on the head portion 32 of the heat sink 30, and the heat sink 30 may be spaced apart from the second side 13 of the piezoelectric-vibrator assembly 10 via the acoustic-absorption layer 40.

In addition, the front end of the heat sink 30 may also be processed into a fin shape. More specifically, as shown in FIG. 1, the head portion 32 of the heat sink 30 may have a plurality of heat-dissipation portions 322 extending toward the piezoelectric-vibrator assembly 10. The plurality of heat-dissipation portions 322 may be spaced apart from each other. The acoustic-absorption layer 40 may include an acoustic-absorption protrusion 41 disposed or inserted into a gap between every two adjacent heat-dissipation portions 322. In this way, the front end of the heat-dissipation portion 322 may be disposed close to the piezoelectric vibrator 11 to cool down the piezoelectric vibrator 11 better, and the acoustic-absorption protrusion 41 located between the heat-dissipation portions 322 may eliminate a weak noise transmitted from the tail portion 33 to the head portion 32, thereby reducing the interference of the ultrasonic waves on the piezoelectric vibrator 11.

The acoustic-absorption layer 40 may further include a side wall 41. To enhance a structural strength and a compactness of interior components of the ultrasonic transducer 200, the side wall 42 of the acoustic-absorption layer 40 may cover the first surface 331 of the heat sink 30. The end face of the head portion 32 of the heat sink 30 may be defined as a second surface 321. The second surface 321 may be disposed at an end of the head portion 32 facing away from the tail portion 33. An outer face 42a of the first side wall 42 facing away from the tail portion 33 may be substantially parallel to the second surface 321.

The first side wall 42 of the acoustic-absorption layer 40 may be thickened to enhance the absorption effect of the ultrasonic waves refracted out of the heat sink 30 through the first surface 331.

In some embodiments, a distance between the heat sink 30 and the second side 13 of the piezoelectric-vibrator assembly 10 may be defined as $\delta$, which satisfies $0 \le \delta \le 3$ mm. Therefore, in the embodiments in which the ultrasonic waves are weakened by reflected by the tail portion 33 of the heat sink 30 for multiple times and further weakened again by the head portion 32, the heat sink 30 may be disposed closer to the piezoelectric-vibrator assembly 10, so as to reduce the interference on the ultrasonic waves and improve the heat-dissipation performance.

When choosing the material for the heat sink 30 and the acoustic-absorption layer 40, acoustic impedances of the heat sink 30 and the acoustic-absorption layer 40 may be set as close to each other as possible, so as to minimize the ultrasonic energy reflection at an interface of the two materials for the heat sink 30 and the acoustic-absorption layer 40.

Thus, in case that the acoustic impedance of the acoustic-absorption layer 40 is close to the acoustic impedance of the heat sink 30, each time the ultrasonic waves pass through the first surface 331 of the tail portion 33 of the heat sink 30, most of the energy may be refracted into the acoustic-absorption layer 40 covering the surface of heat sink 30 and be further consumed by the acoustic-absorption layer 40. Only a small part of the energy may continue to be transmitted at a tail end (including such as the tail portion 33) of the heat sink 30 after being reflected by the first surface 331. After the energy is reflected and refracted for several times at the tail end, few ultrasonic energy that may cause interference signals will continue to be transmitted.

Figure 10:
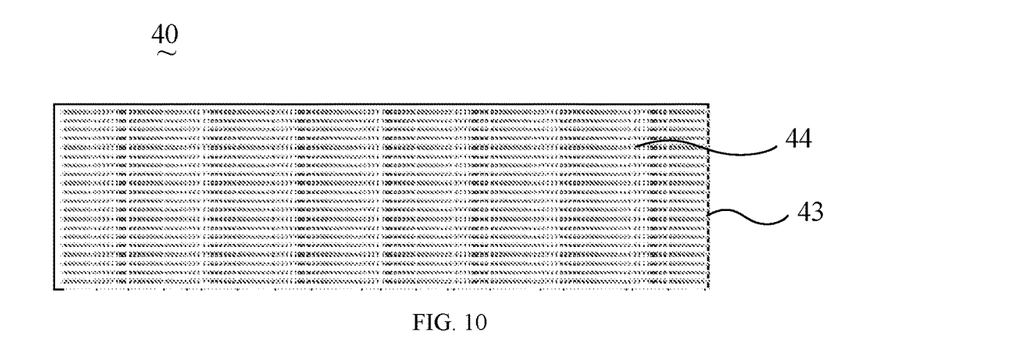
FIG. 10 is a schematic view of the acoustic-absorption layer according to some embodiments of the present disclosure.

In some embodiments, as shown in FIG. 10 the acoustic-absorption layer 40 may include a flexible substrate 43 and particles 44 filled in the flexible substrate 43. The flexible substrate 43 may be made of any material selected from the group consisting of epoxy, polyurethane, and silica gel. The particles may be selected from the group consisting of tungsten powders and lead powders. Based on this, the acoustic-absorption layer 40 may be a composite material prepared by filling a soft substrate with a particle material having a larger gravity, and ultrasonic attenuation may be achieved by damping vibration of particles having larger gravity in the soft substrate. For example, the acoustic-absorption layer 40 may be acquired by filling dense particles such as tungsten powders and lead powders in the soft substrate made of such as epoxy, polyurethane, silica gel, or the like. The heat sink 30 may be made of a thermally-conductive material with low acoustic impedance, such as graphite, aluminum, or the like. In this way, it is possible to adjust a ratio of the material of the acoustic-absorption layer 40 to acquire the acoustic impedance parameters the same or similar to those of the heat sink 30.

An arrow direction in FIG. 1 represents the transmission direction of the ultrasonic waves. When the ultrasonic waves are transmitted to the tail end of the heat sink 30, the ultrasonic waves may be reflected and refracted by the first surface 331. Most of the ultrasonic energy may be refracted into the acoustic-absorption layer 40 and be further absorbed by the acoustic-absorption layer 40. A small part of the energy may be reflected and continue to be transmitted to a side surface of the tail end, and reflected and refracted by the side surface again and further mostly absorbed by the acoustic-absorption layer 40. In this way, the ultrasonic energy may be substantially consumed after multiple reflections between the first surface 331 and the side surface. In some embodiments, among the outer faces 33a of the tail portion 33, at least a surface of the outer faces 33a of the tail portion 33 facing away from the head portion 32 (for example, the first surface 331) may be a polished surface. In this way, after the reflective surface is polished, roughness of the first surface 331 and the side surface of the tail end of the heat sink 30 that are configured to reflect the ultrasonic waves may be much less than wavelengths of the ultrasonic waves, thereby eliminating or reducing the phenomenon of returning ultrasonic noise signals caused by diffuse reflection.

In some embodiments of the present disclosure, as further shown in FIG. 1, the ultrasonic probe 100 may include the ultrasonic transducer 200 as described in the above-mentioned embodiments. The ultrasonic probe 100 may further include a housing 60 and an acoustic window 50. The acoustic window 50 may be connected to the housing 60 at one end of the housing 60. The acoustic window 50 and the housing 60 may cooperatively define a receiving cavity 70, and the ultrasonic transducer 200 may be received in the receiving cavity 70. The ultrasonic probe 100 may have the advantages of the above-mentioned ultrasonic transducer 200, which will not be repeated here.

In some embodiments of the present disclosure, an ultrasonic detection apparatus may be disclosed. The ultrasonic detection apparatus may include the ultrasonic probe 100 as described in the above-mentioned embodiments. Therefore, the ultrasonic detection apparatus including the above-mentioned ultrasonic probe 100 may present the detection result more accurately, a detection accuracy may be higher, and a service life may be longer.

Figure 11:
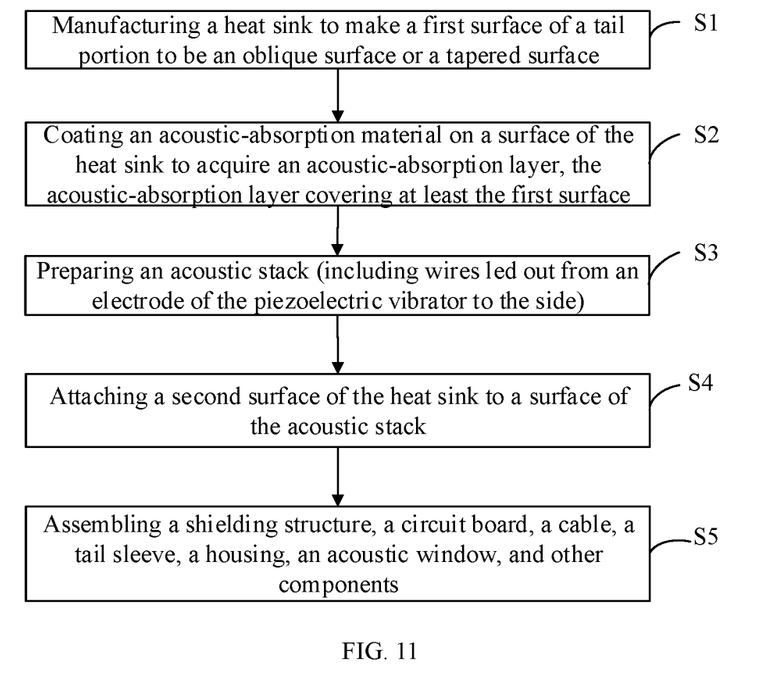
FIG. 11 is a flow chart of a method for manufacturing an ultrasonic probe according to some embodiments of the present disclosure.

FIG. 11 is flow chart of a method for manufacturing the ultrasonic probe 100 according to some embodiments of the present disclosure. The method may include actions executed by the following blocks.

At block S1, firstly, a heat sink 30 may be prepared. The heat sink 30 may be made of materials having a higher thermal conductivity. The heat sink 30 may occupy a large space in an internal space of the ultrasonic probe 100 to absorb and disperse heat generated during the operation of the one or more piezoelectric vibrators 11. The first surface 331 of the tail portion 33 of the heat sink 30 may be processed into an oblique surface or a tapered surface that may be inclined as a whole. The oblique surface or the tapered surface should have a small inclination angle with respect to the central axis of the body 31, such that the ultrasonic waves may be reflected and refracted by the inclined sub-surface for multiple times.

At block S2, then, an acoustic-absorption layer 40 may be coated on a surface of the heat sink 30. The acoustic-absorption layer 40 may be prepared according to or based on an acoustic impedance of the heat sink 30, such that the acoustic-absorption layer 40 may have the acoustic impedance as close as possible to that of the heat sink 30. In this way, when the ultrasonic waves are transmitted to an interface between the heat sink 30 and the acoustic-absorption layer 40, most of the energy may be refracted into the acoustic-absorption layer 40 and absorbed by the acoustic-absorption layer 40. A very small part of the energy may be reflected at the interface.

The acoustic-absorption layer 40 should cover at least cover the oblique surface of the tail portion 33 of the heat sink 30. Besides, the portion of the acoustic-absorption layer 40 covering the oblique surface may have a sufficient thickness to fully absorb the ultrasonic energy refracted into the acoustic-absorption layer 40. In order to achieve a better effect, the acoustic-absorption layer 40 may also cover a side wall of the heat sink 30. In this way, most of the ultrasonic energy transmitting to the side wall of the heat sink 30 may be refracted into the acoustic-absorption layer 40 and be further absorbed by the acoustic-absorption layer 40. Whether a surface of the front end of the heat sink 30 needs to be covered with a thinner acoustic-absorption layer 40 may be determined according to the defects inside of the heat sink 30 and the application of the probe.

At block S3, an acoustic stack of the ultrasonic probe 100 may be prepared according to a conventional process. The acoustic stack may include the piezoelectric vibrator 11 and the acoustic matching layer 20 disposed on a front side (the first side 12) of the piezoelectric vibrator 11, and may also include acoustic functional layers disposed on a rear side (the second side 13) of the piezoelectric vibrator 11, such as a tuning layer, a dematching layer, an acoustic amplification layer, or the like. Each circuit of the piezoelectric vibrator 11 may be led out from the side of the piezoelectric vibrator 11 without affecting the transmission of the ultrasonic signals.

At block S4, the front end face of the heat sink 30 in the block S2 may be attached to or bonded to a surface of the acoustic stack at the rear end of the piezoelectric vibrator 11 in the block S3. The front end face of the heat sink 30 may be directly a surface of the heat sink 30 (that is, the surface of the heat sink 30 free of being covered by the acoustic-absorption layer 40), or may be a surface of the heat sink 30 covered by the acoustic-absorption layer 40 of a certain thickness. The two surfaces that may be bonded to each other may have good flatness to ensure that an adhesive layer may be thin enough and may not affect the transmission of the ultrasonic waves and the heat.

At block S5, the assembly of a shielding structure, a circuit board, a cable, a tail sleeve, a housing 60, an acoustic window 50 and other components may be completed. The heat sink 30 may also be further connected to the housing 60, the cables, and other components, to further diffuse the heat outward, thereby forming the ultrasonic probe 100 with good internal heat dissipation.

The related manufacturing process of the ultrasonic probe 100 according to some embodiments of the present disclosure may be not complicated to implement, as long as the front end face of the heat sink 30 covered with or wrapped by the acoustic-absorption layer 40 according to some embodiments of the present disclosure may be directly bonded to the surface of the acoustic stack of the ultrasonic transducer.

In the description of the embodiments of the present disclosure, it should be understood that, the orientation or positional relationships indicated by the terms "center", "longitudinal", "transverse", "length", "width", "thickness", "upper", "lower", "front", "rear", "left", "right", "vertical", "horizontal", "top", "bottom", "inner", "outer", "clockwise", "counterclockwise", or the like, are based on the orientation or positional relationship shown in the drawings, and are merely for convenience of description and for simplifying description, rather than implying or indicating that the device or the component must have a particular orientation or constructed and operated in a particular orientation, and thus these terms cannot to be construed as limiting the present disclosure. In addition, the features defined with "first", "second", or the like may explicitly or implicitly include one or more of the features. In the description of the present disclosure, it should be noted that, "a plurality of" means two or more, unless specified otherwise.

In the description of the present specification, the description with reference to the terms "one embodiment", "some embodiments", "illustrative embodiment", "example", "specific example", or "some examples", or the like, means that a specific feature, structure, material, or characteristic described in connection with the embodiment or example is included in at least one embodiment or example of the present disclosure. Thus, the illustrative descriptions of the terms throughout this specification are not necessarily referring to the same embodiment or example of the present disclosure. Furthermore, the specific features, structures, materials, or characteristics may be combined in any suitable manner in one or more embodiments or examples.

Although some embodiments of the present disclosure have been shown and described above, however, it can be understood that the above-mentioned embodiments may be exemplary and should not be construed as limiting the present disclosure. Those skilled in the art may make various changes, modifications, substitutions and modifications to the embodiments described above within the scope of the present disclosure.

What is claimed is:

1. An ultrasonic transducer, comprising:
a piezoelectric-vibrator assembly, having a first side and a second side opposite to the first side and comprising one or more piezoelectric vibrators, wherein the one or more piezoelectric vibrators extend from the first side to the second side;
an acoustic matching layer, arranged on the first side of the piezoelectric-vibrator assembly;
a heat sink, arranged on the second side of the piezoelectric-vibrator assembly and comprising:
a body, having a central axis;
a head portion, disposed at one end of the body and facing towards the piezoelectric-vibrator assembly; and
a tail portion, disposed at another end of the body opposite to the head portion and facing away from the piezoelectric-vibrator assembly, wherein the central axis extends in a direction from the head portion to the tail portion; the tail portion comprises a first surface disposed at one side of the tail portion facing away from the head portion, the first surface is an oblique surface or a tapered surface, and an angle between the first surface and the central axis is an acute angle; and
an acoustic-absorption layer, covering at least the first surface,
wherein the tail portion further comprises a side wall connected to the first surface, the first surface is configured to refract a part of ultrasonic waves to the acoustic-absorption layer and reflect another part of the ultrasonic waves to the side wall; and
the acoustic-absorption layer is configured to receive the part of the ultrasonic waves refracted by the first surface.

2. The ultrasonic transducer as claimed in claim 1, wherein the oblique surface comprises at least one inclined sub-surface, and an angle between each of the at least one inclined sub-surface and the central axis of the body is an acute angle.

3. The ultrasonic transducer as claimed in claim 1, wherein the oblique surface comprises a pair of inclined sub-surfaces intersecting with each other at a straight line and gradually extending away from each other in a direction from the tail portion to the head portion, an angle between the pair of inclined sub-surfaces is an acute angle, and an angle between each of the pair of inclined sub-surfaces and the central axis of the body is an acute angle.

4. The ultrasonic transducer as claimed in claim 1, wherein the oblique surface is a pyramid surface comprising a plurality of sub-surfaces, and an angle between each of the plurality of sub-surfaces and the central axis is an acute angle.

5. The ultrasonic transducer as claimed in claim 1, wherein the tapered surface is a conical surface having a generatrix, an angle between the generatrix of the conical surface and the central axis is less than 90 degrees.

6. The ultrasonic transducer as claimed in claim 1, wherein the tail portion comprises an outer face, the outer face of the tail portion comprises the first surface and another surface;
the acoustic-absorption layer covers the first surface and the another surface of the tail portion; or
the acoustic-absorption layer covers the outer face of the tail portion, an outer face of the body, and a side wall of the head portion; or
the acoustic-absorption layer covers an outer face of the heat sink.

7. The ultrasonic transducer as claimed in claim 6, wherein the heat sink is made of any material selected from the group consisting of monocrystal alumina, monocrystal silicon, and monocrystal silicon carbide.

8. The ultrasonic transducer as claimed in claim 1, wherein a distance between the second side of the piezoelectric-vibrator assembly and the heat sink is defined as $\delta$, wherein $0 \leq \delta \leq 3$ mm.

9. The ultrasonic transducer as claimed in claim 1, wherein the head portion comprises a second surface disposed at an end of the head portion facing away from the tail end, the acoustic-absorption layer further covers the second surface, and the second surface is spaced from the second side of the piezoelectric-vibrator assembly via the acoustic-absorption layer.

10. The ultrasonic transducer as claimed in claim 9, wherein the head portion comprises a plurality of heat-dissipation portions extending toward the piezoelectric-vibrator assembly, the plurality of heat-dissipation portions are spaced apart from each other, and the acoustic-absorption layer comprises an acoustic-absorption protrusion disposed in a gap defined between every two adjacent heat-radiating portions.

11. The ultrasonic transducer as claimed in claim 1, wherein the acoustic-absorption layer comprises a side wall covering the first surface of the heat sink, and the head portion further comprises a second surface disposed at an end facing away from the tail portion, the side wall comprises an outer face facing away from the tail portion, and the outer face of the side wall is parallel to the second surface.

12. The ultrasonic transducer as claimed in claim 1, wherein the tail portion comprises an outer face, the outer face comprises the first surface, and at least the first surface of the outer face of the tail portion is a polished surface.

13. The ultrasonic transducer as claimed in claim 1, wherein the acoustic-absorption layer comprises a flexible substrate and particles filled in the flexible substrate;
the flexible substrate is made of any one selected from the group consisting of epoxy, polyurethane, and silicone;
the particles are selected from the group consisting of tungsten powders and lead powders.

14. An ultrasonic probe, comprising:
an ultrasonic transducer, comprising:
a piezoelectric-vibrator assembly, having a first side and a second side opposite to the first side and comprising one or more piezoelectric vibrators, wherein the one or more piezoelectric vibrators extend from the first side to the second side;
an acoustic matching layer, arranged on the first side of the piezoelectric-vibrator assembly;

a heat sink, arranged on the second side of the piezoelectric-vibrator assembly and comprising:
- a body, having a central axis;
- a head portion, disposed at one end of the body and facing towards the piezoelectric-vibrator assembly; and
- a tail portion, disposed at another end of the body opposite to the head portion and facing away from the piezoelectric-vibrator assembly, wherein the tail portion comprises a first surface disposed at one side of the tail portion facing away from the head portion, and the first surface is an oblique surface or a tapered surface; and an acoustic-absorption layer, covering at least the first surface, wherein the tail portion further comprises a side wall connected to the first surface, the first surface is configured to refract a part of ultrasonic waves to the acoustic-absorption layer and reflect another part of the ultrasonic waves to the side wall; and the acoustic-absorption layer is configured to receive the part of the ultrasonic waves refracted by the first surface.

15. The ultrasonic probe as claimed in claim 14, further comprising:
- a housing;
- an acoustic window, connected to the housing, wherein the acoustic window and the housing cooperatively define a receiving cavity, and the ultrasonic transducer is received in the receiving cavity.

16. The ultrasonic probe as claimed in claim 14, wherein the first surface comprises at least one inclined sub-surface, and an angle between each of the at least one inclined sub-surface and the central axis of the body is an acute angle.

17. The ultrasonic probe as claimed in claim 14, wherein the first surface comprises a pair of inclined sub-surfaces intersecting with each other at a straight line and gradually extending away from each other in a direction from the tail portion to the head portion, an angle between the pair of inclined sub-surfaces is an acute angle, and an angle between each of the pair of inclined sub-surfaces and the central axis of the body is an acute angle.

18. The ultrasonic probe as claimed in claim 14, wherein the first surface is a pyramid surface comprising a plurality of sub-surfaces, and an angle between each of the plurality of sub-surfaces and the central axis is an acute angle.

19. The ultrasonic probe as claimed in claim 14, wherein the first surface is a conical surface having a generatrix, an angle between the generatrix of the conical surface and the central axis is less than 90 degrees.

20. An ultrasonic detection apparatus, comprising an ultrasonic probe, and the ultrasonic probe comprising an ultrasonic transducer;

the ultrasonic transducer comprising:
- a piezoelectric-vibrator assembly, having a first side and a second side opposite to the first side and comprising one or more piezoelectric vibrators, wherein the one or more piezoelectric vibrators extend from the first side to the second side;
- an acoustic matching layer, arranged on the first side of the piezoelectric-vibrator assembly;
- a heat sink, arranged on the second side of the piezoelectric-vibrator assembly and comprising:
  - a body, substantially in shape of a column and having a central axis;
  - a head portion, disposed at one end of the body and facing towards the piezoelectric-vibrator assembly; and
  - a tail portion, disposed at another end of the body opposite to the head portion and facing away from the piezoelectric-vibrator assembly, wherein the tail portion comprises a first surface disposed at one side of the tail portion facing away from the head portion, and the first surface is an oblique surface, and an angle between the first surface and the central axis is an acute angle; and an acoustic-absorption layer, covering at least the first surface, wherein the tail portion further comprises a side wall connected to the first surface, the first surface is configured to refract a part of ultrasonic waves to the acoustic-absorption layer and reflect another part of the ultrasonic waves to the side wall; and the acoustic-absorption layer is configured to receive the part of the ultrasonic waves refracted by the first surface.

* * * * *